United States Patent
Lee et al.

(10) Patent No.: US 7,132,452 B2
(45) Date of Patent: Nov. 7, 2006

(54) TOPICAL FORMULATION HAVING EFFECTS ON ALLEVIATING PAIN/INFLAMMATION CAUSED BY HERPES VIRUS INFECTION

(76) Inventors: Fang-Yu Lee, 1191 Sec. 1, Chung Shan Road, Tachia, Taichung (TW); Shan-Chiung Chen, No. 24 Tungan Street, Chungyang Li 6th Ling, Fengyuan City, Taichung (TW); Bin-Ken Chen, No. 224 Darna Road, Chungsan Village, Waipu Shiang, Taichung (TW); Chiung-Ju Tsai, 3rd Fl., No. 86, Boai Road, Kejuang Li, Yuanli Jen, Miaoli (TW); Yen-Ling Yi, No. 367, Shuentian Road, Dajia Jen,, Taichung (TW); Wei-Liang Lin, 2nd Fl., No. 112-1, Shinshi St., Anle Chiu, Keelung (TW)

( * ) Notice: Subject to any disclaimer, the term of this patent is extended or adjusted under 35 U.S.C. 154(b) by 5 days.

(21) Appl. No.: 10/383,525

(22) Filed: Mar. 10, 2003

(65) Prior Publication Data

US 2004/0180066 A1   Sep. 16, 2004

(51) Int. Cl.
*A61K 31/19* (2006.01)
*A61K 31/60* (2006.01)
*A61K 9/14* (2006.01)

(52) U.S. Cl. .............. 514/570; 514/568; 514/165; 514/944; 424/487

(58) Field of Classification Search ............. 514/570, 514/568, 165, 944; 424/487
See application file for complete search history.

(56) References Cited

U.S. PATENT DOCUMENTS 4,184,974 A * 1/1980 Van Leuven ............ 424/618

(Continued)

FOREIGN PATENT DOCUMENTS

EP   0 405 299 A2 *  1/1991

OTHER PUBLICATIONS

Fraser-Smith et al, 110CA:165746, 1988.*

*Primary Examiner*—Shengjun Wang
(74) *Attorney, Agent, or Firm*—Fei-Fei Chao; Bingham McCutchen LLP

(57) ABSTRACT

The present invention provides a topical formulation containing NSAID, particularly diclofenac. The topical formulation is particularly useful for alleviating pain/inflammation associated with infection caused by herpes virus, especially herpes simplex virus (HSV) and varicella-zoster virus (VZV). Similar relief can be achieved where diclofenac is replaced with another non-steroidal anti-inflammatory drug (NSAID), which includes, without limitation, etodolac, ketorolac, bromfenac, diflunisal, ibuprofen, fenoprofen, ketoprofen, naproxen, suprofen, meclofenamate, mefenamic acid, piroxicam, meloxicam, indomethacin, sulindac, phenylbutazone, oxyphenbutazone, and tolmetin. The topical formulation is further characterized by its fast relief on pain and/or inflammation associated with infection caused by herpes virus, i.e., a complete relief in no more than seven (7) days after the application of the topical formulation on skins of patients.

3 Claims, 1 Drawing Sheet

U.S. PATENT DOCUMENTS

| | | |
|---|---|---|
| 4,215,113 A | 7/1980 | Eriksson et al. |
| 4,473,584 A | 9/1984 | Heckler |
| 4,477,468 A | 10/1984 | Heckler |
| 4,711,906 A | 12/1987 | Von Stetten et al. |
| 5,098,716 A | 3/1992 | Embro |
| 5,294,440 A * | 3/1994 | Jack et al. ............... 424/78.05 |
| 5,514,667 A * | 5/1996 | Cullis-Hill .................. 514/54 |
| 5,658,946 A * | 8/1997 | Majeti ...................... 514/493 |
| 5,747,070 A | 5/1998 | Majeti |
| 5,753,270 A * | 5/1998 | Beauchamp et al. ........ 424/667 |
| 5,883,115 A | 3/1999 | Santus et al. |
| 5,977,088 A * | 11/1999 | Harper et al. ................. 514/54 |
| 6,090,368 A | 7/2000 | Zia et al. |
| 6,368,618 B1 | 4/2002 | Jun et al. |
| RE37,727 E | 6/2002 | Hind |
| 6,420,394 B1 | 7/2002 | Supersaxo |

\* cited by examiner

TOPICAL FORMULATION HAVING EFFECTS ON ALLEVIATING PAIN/INFLAMMATION CAUSED BY HERPES VIRUS INFECTION

FIELD OF THE INVENTION

The present invention relates to a topical formulation containing an NSAID, most favorably, diclofenac. Other NSAIDs include, without limitation, etodolac, ketorolac, bromfenac, diflunisal, ibuprofen, fenoprofen, ketoprofen, naproxen, suprofen, meclofenamate, mefenamic acid, piroxicam, meloxicam, indomethacin, sulindac, phenylbutazone, oxyphenbutazone, and tolmetin. The topical formulation is particularly useful for alleviating pain/inflammation associated with infection caused by herpes virus, especially herpes simplex virus (HSV) and varicella-zoster virus (VZV).

BACKGROUND OF THE INVENTION

Non-steroidal anti-inflammatory drugs (NSAIDs) are among the most widely used drugs, probably due to their therapeutic properties as anti-inflammatories, analgesics, anti-pyretics, and anti-thrombolics and are used to treat a variety of clinical conditions manifesting such symptoms as pain, inflammation, fever, and to treat and prevent atherosclerosis.

While these drugs are highly effective, oral administration of many NSAIDs can cause serious adverse effects such as gastrointestinal bleeding and ulceration, liver and kidney damages, and central nervous system and cutaneous disturbances, particularly after extended use. Therefore, in an effort to minimize the adverse effects associated with oral administration, non-oral delivery of NSAIDs has been extensively investigated in recent years.

Transdermal delivery, in particular, is an attractive option because it avoids the hepatic first-pass metabolism, reduces the side effects associated with oral administration, is associated with higher patient compliance and, in some cases, enhances therapeutic efficacy of the drug.

Transdermal delivery of NSAIDs is particularly useful for treatment of rheumatoid arthritis and related conditions, which are characterized by painful and swollen joints due to inflammation in the musculoskeletal tissues of the joints. However, although topical administration of certain NSAIDs has been shown to deliver the drug to the local musculoskeletal tissues of joints where arthritic conditions often develop, due to the low solubility of NSAIDs in water, the effectiveness of topical administration of NSAIDs is limited by the inability of these drugs to permeate the skin.

NSAIDs are weak acid. There are roughly nine major classes of NSAIDs, which are salicylate derivatives (such as acetosalicylate [aspirin]), propionic acid derivatives (such as ibuprofen), aniline derivatives (such as aminophenolacetaminophen [tylenol]), pyrazole derivatives (such as phenylbutazone), N-arylanthranilic acid (or fenamates) derivatives (such as meclofenamate), indole derivatives (such as indomethacin), acetic acid derivatives (such as diclofenac), oxicam derivatives (such as piroxicam), and miscellaneous others (such as celecoxib).

Among the NSAIDs, diclofenac, which is 2-(2,6-dichloro-anilino)-phenyl-acetic acid, is particularly known for its role as an anti-rheumatic agent for treatment of rheumatoid arthritis. Diclofenac belongs to the acetic acid class of NSAID. Due to its relatively low solubility in water, an aqueous injection solution of diclofenac is difficult to achieve.

U.S. Pat. No. 4,711,906 discloses a liquid diclofenac preparation where a better dissolution of the diclofenac is obtained when a local anesthetic, lidocaine, is added. This liquid diclofenac preparation is particularly suitable for use as injection solution.

Another NSAID similar to diclofenac and also belongs to the acetic acid class of NSAIDs is ketorolac. Ketorolac is comparable to opioids in terms of providing pain relief. For example, the overall analgesic effect of 30 mg of ketorolac is equivalent to that of 6 to 12 mg of Morphine.

Ketorolac is (±)-5-benzoyl-2,3-dihydro-1H-pyrrolizine-1-carboxylic acid. It is a derivative of pyrrolizine carboxylic acid and is structurally related to tolmetin and zomepirac. Like diclofenac, the free acid form of ketorolac has very low solubility in water. The most commonly used salt form of ketorolac is ketorolac tromethamine, which is much more water soluble than the free acid form of ketorolac.

Although NSAIDs are widely used as anti-inflammatories and analgesics, the use of NSAIDs in alleviating symptoms associated with herpes virus infection is largely unexplored. Herpetic infections are highly contagious skin eruptions or lesions, characterized by a cluster of small blisters or watery vesicles. The lesions are caused by an acute viral infection. The virus is from the genus *Herpesvirus*.

The herpesviruses comprise a large family of double stranded DNA viruses. The herpesvirus family can be divided into three subfamilies (i.e., α, β, and γ) based upon a number of biological properties such as host range and tropism, viral life cycle, and viral persistence and latency. Eight of the herpesviruses, herpes simplex virus types 1 and 2 (HSV-1 and HSV-2), varicella zoster virus (VZV), human cytomegalovirus (HCMV), Epstein-Barr virus (EBV), and human herpes viruses 6, 7, and 8 (HHV-6, HHV-7, and HHV-8), have been shown to infect humans.

Among the herpesviruses, the two commonly known viruses are herpes simplex virus types 1 and 2, referred to as HSV1 and HSV2 and varicella-zoster virus (VZV). HSV1 causes orofacial lesions, commonly known as fever blisters or cold sores. These lesions most commonly appear on the lips, but may appear on the face, in the mucous membrane lining of the oral cavity, in the eye and nose, and occasionally on the trunk of hands. Infections of the mouth are designated with the term herpes labialis, also called cold sore (feverblister). Other parts of the face can also be affected and the infections thereof are referred to as facial herpes simplex. The infection can also manifest itself on other parts of the body. Approximately 30% of the United States population suffer from recurrent episodes of HSV1. HSV2, which is less common than HSV1, causes genital lesions. Conversely, genital herpes is caused in about 30% of cases by HSV1.

Varicella-zoster virus (VZV) causes varicella, commonly known as chicken pox, and herpes zoster, commonly known as shingles. Shingles affects the skin and nerves and is characterized by groups of small blisters or lesions appearing along certain nerve segments. The lesions are most often seen on the back and may be preceded by a dull ache in the affected site.

Once an individual has been infected with the herpes virus, the virus will thereafter remain latently in the body. In latent state, the virus is situated in nerve cell bodies in the ganglia. Due to particular stimuli, such as influenza infection, other respiratory disorders, gastrointestinal infections, stress, fatigue, menstruation, pregnancy, allergy, sunlight, or fever, the latent virus can be activated and travel from the ganglia along the well-defined nerve paths to the skin surface and there multiply and cause the symptoms.

There is no treatment known to kill the herpes virus at this time. Most of the available treatments can only help to accelerate the healing of the lesions and the associated symptoms, but have not been shown to be efficacious in the treatment of herpes virus infections.

The best known treatment for herpes virus infections at this time is probably Zovirax.RTM. Ointment (Glaxo Wellcome), which contains the active ingredient acyclovir. Acyclovir, 9-(2-hydroxyethoxymethyl), is a purine nucleoside analogue targeting viral encoded DNA polymerase. Other purine nucleoside analogues which are commercially available for treating herpes virus infections include ganciclovir (Roche) and foscarnet (Astra). Although effective, these purine nucleoside analogues are poorly soluble in water and demonstrate low bioavailability. These, accompanying the relative long recovery time required (i.e., generally takes longer than 2 weeks for patients to recover) and high prescription cost, make the drugs less attractive to the patients.

Other commonly known anti-viral drugs for treatment of herpes virus include foscarnet (U.S. Pat. No. 4,215,113); stannous salt, such as stannous fluoride (U.S. Pat. No. 5,098,716); and sulphated polysaccharides, such as dextran sulphate and pentosan polysulphate. Recently, U.S. Pat. No. RE37,727 discloses a method for treating nerves injury pain associated with shingles by using a local anethetic agent, lidocaine.

NSAIDs are not widely known for treatment of viruses, notwithstanding herpes viruses. U.S. Pat. Nos. 4,473,584 and 4,477,468 disclose a process for treating HSV1 and HSV2 infection by systemic administration or topical application of flurbiprofen (3-fluoro-4-phenylhydratropic acid) or a salt or ester thereof. U.S. Pat. No. 5,514,667 discloses a topical preparation for treating herpes virus infections which combines an anti-viral drug, such as foscarnet, suramin, polysulphated polysaccharides, polysulphated polymers, purine nucleoside analogues, with a potentiating drug which can be an NSAID. U.S. Pat. No. 5,747,070 discloses a treatment for herpes infections which combines stannous salt with another therapeutic agent, such as an NSAID.

The present invention provides a topical formulation containing an NSAID, preferably diclofenac, to provide fast and effective treatment for alleviating symptoms relating to HSV and VZV infections, including inflammation and/or pain caused by HSV and VZV infections. In comparing with the topical treatment by acyclovir, the topical formulation of the present invention reduces the recovery time from about two (2) weeks when acyclovir is applied, to about one (1) week when a topical preparation using the topical formulation of the present invention is applied.

SUMMARY OF THE INVENTION

The present invention provides a topical formulation containing diclofenac, including, without limitation, diclofenac acid, diclofenac sodium, diclofenac potassium, diclofenac diethylamine, diclofenac triethanolamine, and diclofenac tromethamine. The topical formulation is especially used for treatment with pain and/or inflammation associated with infection caused by herpes virus, including, but not limited to, herpes simplex virus (HSV) and/or varicella-zoster virus (VZV). Also, the topical formulation does not contain an anti-viral drug. Optionally, the topical formulation may or may not contain a local anesthetic agent. Examples of an anti-viral drug includes purine nucleoside analogues (e.g., acyclovir, valacyclovir, and ganciclovir); foscarnet; suramin; stannous salt, such as stannous fluroide; and sulphated polysaccharides, such as dextran sulphate and pentosan polysulphate.

The topical formulation is preferably delivered as a liquid or semi-liquid topical preparation. Examples of the topical preparation include, without limitation, solution, suspension, gel, emugel, cream, ointment, lotion, and transdermal patch.

The preferred amount of diclofenac used in the topical formulation is about 0.1–10% by weight (w/w) or by volume (w/v) of the entire topical formulation.

The topical formulation of the present invention is further characterized by its fast recovery effect (i.e., no more than 7 days) on skin blisters/lesions caused by herpes virus infection.

Optionally, the diclofenac in the topical formulation is replaced with a non-diclofenac non-steroidal anti-inflammatory drug (NSAID), which includes, without limitation, etodolac, ketorolac, bromfenac, diflunisal, ibuprofen, fenoprofen, ketoprofen, naproxen, suprofen, meclofenamate, mefenamic acid, piroxicam, meloxicam, indomethacin, sulindac, phenylbutazone, oxyphenbutazone, and tolmetin. The preferred NSAID is ketorolac, such as a free acid form of ketorolac or ketorolac tromethamine.

The present invention also provides a method for treating patients with pain and/or inflammation associated with infection caused by herpes virus, such as herpes simplex virus (HSV) and/or varicella-zoster virus (VZV). The method includes topically applying to the patients an effective amount of the topical formulation containing diclofenac, including, without limitation, diclofenac acid, diclofenac sodium, diclofenac potassium, diclofenac diethylamine, diclofenac triethanolamine, and diclofenac tromethamine. The topical formulation does not contain an anti-viral drug. Optionally, the topical formulation may or may not contain a local anesthetic agent. The effective amount of the diclofenac is about 0.1~10% by weight (w/w) or by volume (w/v) of the entire topical formulation. The topical formulation of the present invention, when applies to patients with skin blisters/lesions caused by herpes virus infection, fasten the skin recovery to no more than 7 days.

Optionally, the diclofenac is replaced with a non-diclofenac non-steroidal anti-inflammatory drug (NSAID), such as etodolac, ketorolac, bromfenac, diflunisal, ibuprofen, fenoprofen, ketoprofen, naproxen, suprofen, meclofenamate, mefenamic acid, piroxicam, meloxicam, indomethacin, sulindac, phenylbutazone, oxyphenbutazone, and tolmetin. The preferred NSAID is ketorolac, such as a free acid form of ketorolac or ketorolac tromethamine.

DETAILED DESCRIPTION OF THE INVENTION

Figure 1:
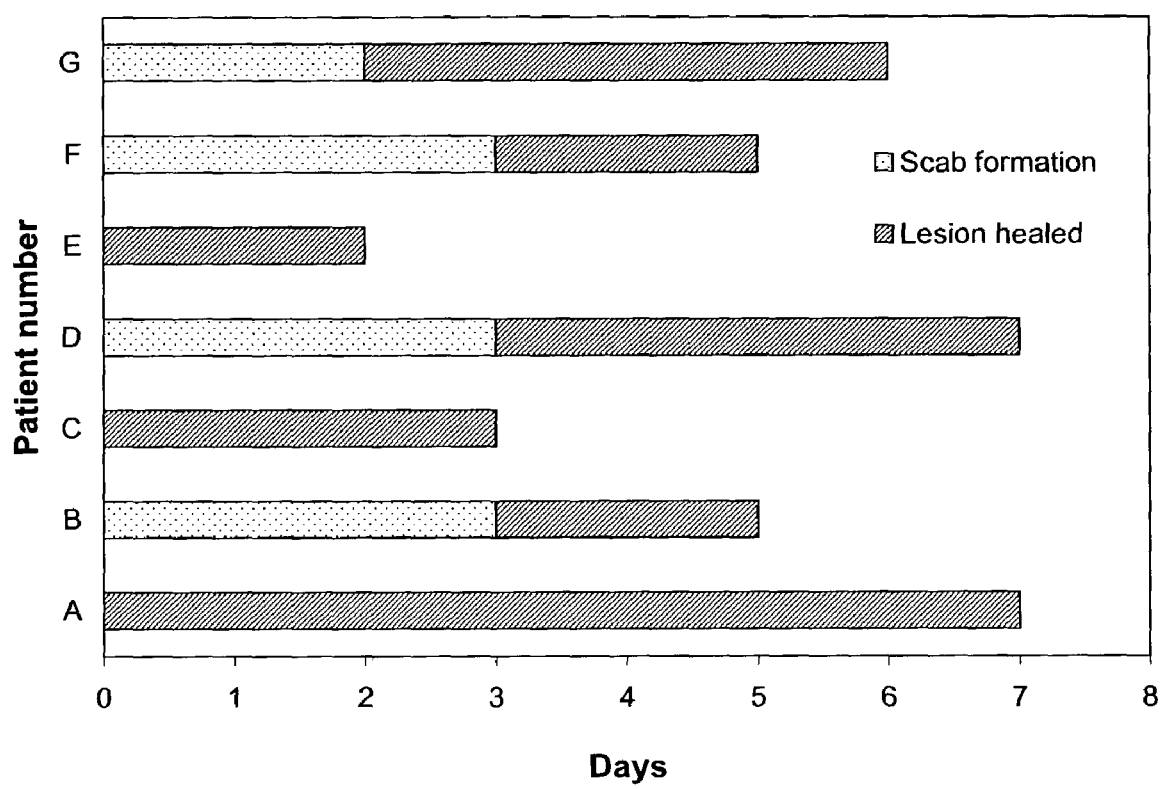
FIG. 1 shows the results of patients infected with herpes viruses after being topically treated with the topical formulation of the present invention in the form of a gel for seven (7) days. ▦ represents the period of time (days) when a scab was formed. ▮ represents the period of time (days) when the scab is automatically peeled off from the skin, an indication that the lesions were cured.

The topical formulation of the present invention has been examined by the following instrumentations to ensure quality:

High Performance Liquid Chromatography (HPLC): The topical formulation can be characterized and purified by HPLC. Alternatively, the content or purity of the topical formulation can be determined by HPLC. For a given column packing, solvent system, and flow rate, the composition tends to elute to a certain degree from an analytical or preparative HPLC column.

UV Spectroscopy: the UV spectroscopy can be used to perform qualitative analysis of the topical formulation.

Transdermal Absorption Test: the transdermal absorption of the topical formulation can be determined using the transdermal diffusion measurement instrument. For example, the accumulative transdermal absorption is determined by 3M 9728 Membranes.

pH Determination: pH of the topical formulation is determined by a pH-meter.

The topical formulations used in the present invention are particularly suitable for formulations as topical preparations. Formulations suitable for topical administration include liquid or semi-liquid preparations suitable for penetration through the skin to the site of where treatment is required. Examples of liquid and semi-liquid preparations include, but are not limited to, topical solutions, liniments, lotions, creams, ointment or paste, gel, and emugel. Other topical ingredients used in the topical formulation are in general those commonly used and generally recognized by person skilled in the art of topical formulation.

Topical solution of the present invention may contain aqueous or oily solution or suspensions. They may be prepared by dissolving the pharmaceutical compound in a suitable aqueous solution which may also contain a bactericidal agent, a fungicidal agent, or any other suitable preservative, and may preferably include a surface active agent. Suitable solvents for the preparation of an oily solution include glycerol, diluted alcohol, and propylene glycol. Optionally, L-menthol may be added to the topical solution.

Lotions and liniments include those suitable for application to the skin containing a sterile aqueous solution and optionally, a bactericide. They may also include an agent to hasten drying and cooling of the solution on the skin, such as alcohol or acetone. They may further include a moisturizer, such as glycerol, or an oil, such as castor oil or arachis oil.

Cream, ointments, or pastes, are semi-solid formulations made by mixing the pharmaceutical with a greasy or non-greasy base. The topical formulation is in finely-divided or powdered form and may be alone or in a aqueous or non-aqueous solution or suspension. The topical formulation may be mixed with the greasy or non-greasy base with the aid of suitable machinery. The base may contain hydrocarbons. Examples of the hydrocarbons include, but are not limited to, hard, soft, or liquid paraffin, glycerol, beeswax, a metallic soap, a mucilage, an oil of natural origin (such as almond, corn, arachis, castor or olive oil), wool fat or its derivative, a fatty acid (such as stearic acid or oleic acid), or a combination thereof. The formulation may also contain a surface active agent, such as an anionic, cationic or non-ionic surfactant. Examples of the surfactants include, but are not limited to, sorbitan esters or polyoxyethylene derivatives thereof (such as polyoxyethylene fatty acid esters) and carboxypolymethylene derivatives thereof (such as carbopol). Suspending agents such as natural gums, cellulose derivatives inorganic materials such as silicaceous silicas, and other ingredients such as lanolin, may also be included. For ointment, polyethylene glycol 540, polyethylene glycol 3350, and propylene glycol may also be used to mixed with the topical formulation.

A gel or emugel formulation includes any gel forming agent commonly used in the pharmaceutical gel formulations. Examples of gel forming agents are cellulose derivatives such as methyl cellulose, hydroxyethyl cellulose, and carboxymethyl cellulose; vinyl polymers such as polyvinyl alcohols, polyvinyl pyrrolidones; carboxypoly-methylene derivatives such as carbopol. Further gelling agents that can be used for the present invention are pectins and gums (such as gum arabic and tragacanth, alginates, carrageenates, agar and gelatin). The preferred gelling agent is carbopol. Furthermore, the gel or emugel formulation may contain auxiliary agents commonly used in the kind of formulations such as preservatives, antioxidants, stabilizers, colorants, and perfumes.

The following examples are illustrative, but not limiting the scope of the present invention. Reasonable variations, such as those occur to reasonable artisan, can be made herein without departing from the scope of the present invention.

EXAMPLE 1

Preparation of A Gel Containing Diclofenac Acid

A gel containing diclofenac acid for topical treatment of pain/inflammation caused by HSV and/or VZV infection was prepared as follows:

| Ingredients | Weight (g) |
| --- | --- |
| Diclofenac Acid | 10 |
| L-Menthol | 10 |
| Propylene glycol | 200 |
| Triethanolamine | 20 |
| Carboxypolymethylene (Carbopol) | 15 |
| Isopropyl Alcohol | 250 |
| Purified Water | 375 |
| Total Weight | 880 |

The method for preparing the gel was as follows:

1. Carbopol 15 g was mixed with isopropyl alcohol 150 g. Then, purified water 375 g was added to the mixture and mixed well so that Carbopol and isopropyl alcohol dissolved in the purified water.

2. Diclofenac acid 10 g, propylene glycol 200 g, and isopropyl alcohol 50 g were mixed together and dissolved.

3. L-menthol 10 g was added to isopropyl alcohol 50 g and mixed so that L-menthol dissolved in the isopropyl alcohol.

4. Mixtures obtained from steps 2 and 3 were added to the mixture from step 1 and mixed until they were evenly distributed. Then, triethanolamine 20 g was added to the mixture and mixed well to obtain the topical formulation to be used in the present invention in the form of a gel.

EXAMPLE 2

Preparation of A Gel Containing Diclofenac Acid

A gel containing diclofenac acid for topical treatment of pain/inflammation caused by HSV and/or VZV infection was prepared from the following ingredients:

| Ingredients | Weight (g) |
| --- | --- |
| Diclofenac Acid | 296.15 |
| L-Menthol | 200 |

-continued

| Ingredients | Weight (g) |
|---|---|
| Propylene Glycol | 4000 |
| Triethanolamine | 400 |
| Carboxypolymethylene (Carbopol) | 200 |
| Isopropyl Alcohol | 6900 |
| Purified Water | 7669.51 |
| Total Weight | 19665.66 |

The topical formulation was prepared as follows:

1. Carbopol 200 g was mixed with isopropyl alcohol 150 g. Then, purified water 7669.51 g was added to the mixture and mixed well so that Carbopol and isopropyl alcohol dissolved in the purified water.

2. Diclofenac acid 296.15 g, propylene glycol 4000 g, and isopropyl alcohol 50 g were mixed together and dissolved.

3. L-menthol 200 g was added to isopropyl alcohol 50 g and mixed so that L-menthol dissolved in the isopropyl alcohol.

4. Mixtures obtained from steps 2 and 3 were added to the mixture from step 1 and mixed until they were evenly distributed. Then, triethanolamine 400 g was added to the mixture and mixed well to obtain the topical formulation to be used in the present invention in the dosage form of a gel.

EXAMPLE 3

Preparation of A Solution Containing Diclofenac Acid

A solution containing diclofenac acid was prepared from the following ingredients:

| Ingredients | Weight (g) or Volume (ml) |
|---|---|
| Diclofenac Acid | 29.615 g |
| L-Menthol | 2 g |
| Alcohol | 5280 ml |
| Purified Water | 2830 ml |
| Total Weight | 8000 ml |

The solution of the present invention was prepared as follows:

1. Diclofenac acid 29.615 g was added to alcohol 4000 g, mixed together, and dissolved.

2. L-menthol 2 g was added to the mixture from step 1 and mixed until dissolved. Purified water was added to and mixed with the mixture to make up a total volume of 8000 ml to obtain the topical formulation to be used in the present invention in the dosage form of a solution.

EXAMPLE 4

Preparation of A Cream Containing Diclofenac Acid

A cream containing diclofenac acid to be used in the present invention was prepared from the following ingredients:

| Ingredients | Weight (g) or Volume (ml) |
|---|---|
| Diclofenac acid | 29.615 g |
| Alcohol | 200 ml |
| Polyoxyethylene Fatty Acid Esters | 200 g |
| Carboxypolymethylene (Carbopol) | 50 g |
| Purified Water | 720.385 g |
| Total Weight | 1000 g |

The cream was prepared as follows:

1. Diclofenac acid 29.615 g was added to alcohol 200 ml and mixed together so that diclofenac acid was dissolved.

2. The mixture from step 1 was added to and mixed with polyoxyethylene fatty acid esters. The mixture was heated and mixed until dissolved.

3. Carbopol 50 g was added to and mixed with purified water 500 g to obtain a homogeneous solution.

4. The mixtures from steps 2 and 3 were mixed evenly and added to purified water 220.385 g. Then, the mixture was stirred until dissolved evenly to obtain the topical formulation to be used in the present invention in the dosage form of a cream.

EXAMPLE 5

Preparation of An Ointment Containing Diclofenac Acid

An ointment containing diclofenac acid was prepared from the following ingredients:

| Ingredients | Weight (g) or Volume (ml) |
|---|---|
| Diclofenac acid | 23.434 g |
| Alcohol | 200 ml |
| Polyethylene Glycol 540 | 200 g |
| Polyethylene Glycol 3350 | 646.951 g |
| Propylene Glycol | 139.615 g |
| Total Weight | 1000 g |

The ointment was prepared as follows:

1. Diclofenac acid 23.434 g was added to alcohol 200 ml and mixed until diclofenac was dissolved and evenly distributed.

2. The mixture from step 1 was added to polyethylene glycol 540 and polyethylene glycol 3350 and heated until the mixture was completely dissolved.

3. The mixture from step 2 was added with propylene glycol and mixed till dissolved evenly to obtain the topical formulation to be used in the present invention in the dosage form of an ointment.

EXAMPLE 6

Preparation of An Emugel Containing Diclofenac Diethylamine

An emugel containing diclofenac diethylamine to be used in the present invention was prepared from the following ingredients:

| Ingredients | Weight (g) |
| --- | --- |
| Diclofenac Acid Diethylamine Salt | 11.6 |
| L-Menthol | 10 |
| Propylene Glycol | 200 |
| Triethanolamine | 20 |
| Carboxypolymethylene (Carbopol) | 15 |
| Isopropyl Alcohol | 150 |
| Purified Water | 343.4 |

The emugel of the present invention was prepared as follows:
1. Diclofenac acid diethylamine salt and propylene glycol were added to purified water 200 g and mixed until they were dissolved and evenly distributed.
2. Carbopol was added to and mixed with isopropyl alcohol 100 g until even distribution. Purified water 143.4 g was added to and mixed with the mixture to dissolve evenly.
3. L-Menthol was added to and mixed with isopropyl alcohol 50 g until evenly dissolved.
4. Mixtures from steps 1, 2, and 3 were added together, mixed, until evenly distributed. Triethanolamine was added and mixed with the mixture to obtain the topical formulation to be used in the present invention in the dosage form of an emugel.

EXAMPLE 7

Preparation of A Gel Containing Diclofenac Sodium

A gel containing diclofenac sodium was prepared from the following ingredients:

| Ingredients | Weight (g) |
| --- | --- |
| Diclofenac Sodium | 10 |
| L-Menthol | 10 |
| Propylene Glycol | 200 |
| Triethanolamine | 20 |
| Carboxypolymethylene (Carbopol) | 15 |
| Isopropyl Alcohol | 250 |
| Purified Water | 375 |
| Total Weight | 880 |

The gel was prepared as follows:
1. Carbopol was added with isopropyl alcohol 150 g and mixed to dissolve evenly. Purified water was added to and mixed with the mixture to dissolve evenly.
2. Diclofenac sodium, propylene glycol, and isopropyl alcohol 50 g were mixed to dissolve.
3. L-Menthol was added with isopropyl alcohol 50 g and mixed to dissolve evenly.
4. Mixtures from steps 2, and 3 were mixed and added to the mixture from step 1 and evenly distributed. Triethanolamine was added to and mixed with the mixture to obtain the topical formulation to be used in the present invention in the dosage form of a gel.

EXAMPLE 8

Preparation of A Lotion Containing Diclofenac Acid

A lotion containing diclofenac acid was prepared from the following ingredients:

| Ingredients | Weight (g) or Volume (ml) |
| --- | --- |
| Diclofenac Acid | 29.615 g |
| Alcohol | 120 ml |
| White soft paraffin | 7.6 g |
| Cetyl Alcohol | 19 g |
| Propylene Glycol | 57 g |
| Methyl Paraben | 1.5 g |
| Propyl Paraben | 0.5 g |
| Sodium Lauryl Sulfate | 3 g |
| Purified Water add to | 1000 g |

The lotion was prepared as follows:
1. Diclofenac acid 29.615 g was dissolved in 120 ml of alcohol.
2. Methyl paraben, propyl paraben, and sodium lauryl sulfate were dissolved in 300 ml of purified water and mixed and heated at about 60° C. until they were dissolved.
3. White soft paraffin, cetyl alcohol, and propylene glycol were heated until completely dissolved.
4. The mixtures from steps 1 and 3 were mixed evenly, then, the mixture from step 2 was added to the mixture to mix evenly. Finally, purified water was added to bring the total weight to 1000 g and mixed evenly to obtain the topical formulation to be used in the present invention in the dosage form of a lotion.

EXAMPLE 9

Preparation of A Gel Containing Diclofenac Sodium

The gel containing diclofenac sodium was prepared from the following ingredients:

| Ingredients | Weight (g) |
| --- | --- |
| Diclofenac Sodium | 29.615 |
| L-Menthol | 20 |
| Propylene glycol | 400 |
| Triethanolamine | 40 |
| Carboxypolymethylene (Carbopol) | 20 |
| Isopropyl Alcohol | 690 |
| Purified Water | 766.9 |
| Total Weight | 1966.515 |

The gel of the present invention was prepared as follows:
1. Carbopol was added with isopropyl alcohol 50 g and mixed to dissolve evenly. Purified water was added to and mixed with the mixture to dissolve evenly.
2. Diclofenac sodium, propylene glycol, and isopropyl alcohol 20 g were mixed until dissolved.
3. L-Menthol was added to and mixed with isopropyl alcohol 50 g until dissolved evenly.
4. Mixtures from steps 2, and 3 were mixed and added to the mixture from step 1 until distributed evenly. Triethanolamine was added to and mixed with the mixture to obtain the topical formulation to be used in the present invention in the dosage form of a gel.

EXAMPLE 10

Preparation of A Gel Containing Ketorolac Acid

A gel containing ketorolac acid was prepared from the following ingredients:

| Ingredients | Weight (g) |
| --- | --- |
| Ketorolac Acid | 10 |
| L-Menthol | 10 |
| Propylene Glycol | 200 |
| Triethanolamine | 20 |
| Carboxypolymethylene (Carbopol) | 15 |
| Isopropyl Alcohol | 250 |
| Purified Water | 375 |
| Total Weight | 880 |

The gel was prepared as follows:

1. Carbopol was added to isopropyl alcohol 150 g until dissolved evenly. Purified water was then added to and mixed with the carbopol-isopropyl alcohol mixture until dissolved evenly.
2. Ketorolac acid, propylene glycol, and isopropyl alcohol 50 g were thoroughly mixed until dissolved evenly.
3. L-Menthol was added to isopropyl alcohol 50 g and mixed until dissolved evenly.
4. Mixtures from steps 2, and 3 were mixed and added to the mixture from step 1 until even distribution. Triethanolamine was added to and mixed with the mixture to obtain the topical formulation to be used in the present invention in the dosage form of a gel.

EXAMPLE 11

Preparation of An Emugel Containing Diclofenac Potassium

An emugel containing diclofenac potassium was prepared from the following ingredients:

| Ingredients | Weight (g) |
| --- | --- |
| Diclofenac Potassium | 11.6 |
| L-Menthol | 10 |
| Propylene Glycol | 200 |
| Triethanolamine | 20 |
| Carboxypolymethylene (Carbopol) | 15 |
| Isopropyl Alcohol | 150 |
| Purified Water | 343.4 |

The topical formulation was prepared as follows:

1. Diclofenac potassium and propylene glycol were added to purified water 200 g and mixed until they were dissolved and evenly distributed.
2. Carbopol was added to and mixed with isopropyl alcohol 100 g until dissolved evenly. Purified water 143.4 g was added to and mixed with the mixture until dissolved evenly.
3. L-Menthol was added to and mixed with isopropyl alcohol 50 g until dissolved evenly.
4. Mixtures from steps 1, 2, and 3 were mixed together until evenly distributed. Triethanolamine was added to and mixed with the mixture to obtain the topical formulation to be used in the present invention in the dosage form of a cream.

EXAMPLE 12

Preparation of A Cream Containing Diclofenac Potassium

A cream containing diclofenac potassium was prepared from the following ingredients:

| Ingredients | Weight (g) or Volume (ml) |
| --- | --- |
| Diclofenac Potassium | 29.615 g |
| Alcohol | 200 ml |
| Polyoxyethylene Fatty Acid Esters | 200 g |
| Carboxypolymethylene (Carbopol) | 50 g |
| Purified Water | 720.385 g |
| Total Weight | 1000 g |

The cream of the present invention was prepared as follows:

1. Diclofenac potassium was added to alcohol 200 ml and mixed together until diclofenac potassium was dissolved.
2. The mixture from step 1 was added to and mixed with polyoxyethylene fatty acid esters. The mixture was heated while mixing until complete dissolution.
3. Carbopol was added to and mixed with purified water 500 g to obtain a homogeneous solution.
4. The mixtures from steps 2 and 3 were mixed evenly and added to purified water 220.385 g. Then, the mixture was stirred until dissolved evenly to obtain the topical formulation to be used in the present invention in the dosage form of a cream.

EXAMPLE 13

Preparation of A Solution Containing Ketorolac Tromethamine

A solution containing ketorolac tromethamine was prepared from the following ingredients:

| Ingredients | Weight (g) or Volume (ml) |
| --- | --- |
| Ketorolac Tromethamine | 30 g |
| L-Menthol | 0.5 g |
| Alcohol | 760 ml |
| Purified Water | 280 ml |
| Total Weight | 1000 ml |

The solution was prepared as follows:

1. Ketorolac tromethamine was added to purified water 150 ml and mixed until complete dissolution.
2. L-menthol was added to alcohol and mixed until dissolved. Then, the mixture from step 1 was added to the L-menthol solution and mixed until dissolved. Purified water was added to the mixture to make up a total volume of 1000 ml to obtain the topical formulation to be used in the present invention in the dosage form of a solution.

EXAMPLE 14

Preparation of A Cream Containing Ketorolac Tromethamine

A cream containing ketorolac tromethamine to be used in the present invention was prepared from the following ingredients:

| Ingredients | Weight (g) or Volume (ml) |
|---|---|
| Ketorolac Tromethamine | 50 g |
| Alcohol | 200 ml |
| Polyoxyethylene Fatty Acid Esters | 200 g |
| Carboxypolymethylene (Carbopol) | 50 g |
| Purified Water | 750 g |
| Total Weight | 1000 g |

The cream was prepared as follows:

1. Ketorolac tromethamine was added to and mixed with purified water 300 ml until dissolution.
2. The mixture from step 1 was added to and mixed with polyoxyethylene fatty acid esters. The mixture was heated while mixing until complete dissolution.
3. Carbopol was added to and mixed with purified water 450 ml to obtain a homogeneous solution.
4. The mixtures from steps 2 and 3 were mixed evenly and added to alcohol. Then, the mixture was stirred until dissolved evenly to obtain the topical formulation to be used in the present invention in the dosage form of a cream.

The following are illustrations of clinical studies using the topical formulation (i.e., a gel) of the present invention as specified in Example 1 above on patients with herpes virus infection. The patients participated in these studies all developed small blisters or lesions on or surrounding the lips due to the infection. Other topical formulations, as demonstrated above, showed similar effects as those described below.

CLINICAL TREATMENT EXAMPLE 1

A male patient A with herpetic infection on the lips was treated topically with the gel of the present invention. The gel had immediate effects on relieving pain and itching caused by the infection. About one week later, scabs were formed and peeled off, with areas of skin returned to normal.

CLINICAL TREATMENT EXAMPLE 2

A female patient B with herpetic infection on the lower lip area, as shown by lesions/blisters, was treated topically with the gel of the present invention. The gel had immediate effects on relieving pain and itching from the patient. On the second day after the application of the gel, the lesions/blisters started to shrink and gradually healed. On the third day, the lesions/blisters began to form scabs. On the fifth day, the scabs began to peel off automatically and the skins showed complete recovery shortly thereafter.

CLINICAL TREATMENT EXAMPLE 3

A female patient C with herpetic infection on the upper lip area, as shown by lesions/blisters, was treated topically with the gel of the present invention. The gel had immediate effects on relieving pain and itching from the patient. On the third day, the lesions/blisters were completely disappeared.

CLINICAL TREATMENT EXAMPLE 4

A male patient D with herpetic infection on the upper lip area, as shown by lesions/blisters, was treated topically with the gel of the present invention. The gel had immediate effect on relieving pain from the patient. On the third day, the lesions/blisters began to form scabs. On the seventh day, the scabs automatically peeled off and the areas of skin were returned to normal.

CLINICAL TREATMENT EXAMPLE 5

A male patient E, with herpetic infection at the corners of the lips by forming lesions/blisters, was treated topically with the gel of the present invention. The gel had immediate effect on relieving pain from the patient. On the second day, the lesions/blisters were completely disappeared.

CLINICAL TREATMENT EXAMPLE 6

A male patient F with herpetic infection on the upper lip area, as shown by lesions/blisters, was treated topically with the gel of the present invention. The gel had immediate soothing effect and relieving pain from the patient. On the third day, the lesions/blisters began to form scabs. On the fifth day, the scabs automatically peeled off, and the lesions/blisters were completely disappeared.

CLINICAL TREATMENT EXAMPLE 7

A male patient G with herpetic infection on the facial skin between the lips and the nose, as shown by lesions/blisters, was treated topically with the gel of the present invention. The gel had immediate soothing effect and relieving pain from the patient. On the second day, the lesions/blisters began to form scabs. On the sixth day, the lesions/blisters were completely disappeared.

The clinical application of the gel of the present invention to patients with herpes virus infection was summarized in Table 1 and FIG. 1:

TABLE 1

Treatment Effects on Patients with Herpes Infection

| Example | Sex | Affected Area | Treatment Effect |
|---|---|---|---|
| A | male | herpetic infection on the lips and the mouth | significant effect on relieving pain and itching; epidermis completely healed within about one week. |
| B | female | herpetic infection on the lower lip | significant effect on relieving pain and itching; lesions/blisters formed scabs at the third day and healed at the fifth day. |
| C | female | herpetic infection on the upper lip | significant effect on relieving pain and itching; healed after about 3 days. |
| D | male | herpetic infection on the upper lip | significant effect on relieving pain; lesions/blisters formed scabs at the third day and healed after about seven days. |

TABLE 1-continued

Treatment Effects on Patients with Herpes Infection

| Example | Sex | Affected Area | Treatment Effect |
|---|---|---|---|
| E | male | herpetic infection at the corners of the lips | significant effect on relieving pain and itching; healed at about two days. |
| F | male | herpetic infection on the upper lip | significant effect on relieving pain; lesions/blisters formed scabs at the third day and healed at about five days. |
| G | male | skin between the lips and the nose | significant effect on relieving pain; lesions/blisters formed scabs at the second day and healed at about six days. |

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. A method for treating skin of patients with pain and/or inflammation associated with lesions/blisters appeared around the lip area caused by herpes virus comprising:

topically applying to said skin of said patients an effective amount of a topical formulation comprising:

diclofenac, L-menthol, propylene glycol, triethanolamine, carboxypolymethylene, isopropyl alcohol, and purified water;

wherein said topical formulation relieves pain and itching caused by said lesions/blisters and forms scabs on said skin of said patients;

wherein said topical formulation does not contain an anti-viral agent; and wherein said topical formulation is in a form of gel.

2. The method according to claim 1, wherein said effective amount of said diclofenac is about 0.1~10% by weight (w/w) or by volume (w/v) of the entire topical formulation.

3. The method according to claim 1, wherein said topical formulation relieves pain and itching and forms scabs in no more than 7 days.

* * * * *